(12) United States Patent
Arvinte et al.

(10) Patent No.: US 7,740,842 B2
(45) Date of Patent: *Jun. 22, 2010

(54) STABLE LIQUID FORMULATIONS OF ANTIBODIES

(75) Inventors: Tudor Arvinte, Riehen (CH); Pierre F Fauquex, Augst (CH)

(73) Assignee: Novartis AG, Basel (CH)

( * ) Notice: Subject to any disclaimer, the term of this patent is extended or adjusted under 35 U.S.C. 154(b) by 632 days.

This patent is subject to a terminal disclaimer.

(21) Appl. No.: 11/338,138

(22) Filed: Jan. 24, 2006

(65) Prior Publication Data

US 2006/0127395 A1 Jun. 15, 2006

Related U.S. Application Data

(63) Continuation of application No. 10/478,630, filed as application No. PCT/EP02/06016 on May 31, 2002, now abandoned.

(30) Foreign Application Priority Data

May 31, 2001 (GB) ................................. 0113179.6

(51) Int. Cl.
*A61K 39/395* (2006.01)
(52) U.S. Cl. .............. 424/130.1; 424/133.1; 424/141.1; 530/387.1
(58) Field of Classification Search ........................ None
See application file for complete search history.

(56) References Cited

U.S. PATENT DOCUMENTS

| | | |
|---|---|---|
| 4,605,691 A | 8/1986 | Balazs et al. |
| 5,783,556 A | 7/1998 | Clark et al. |
| 5,908,826 A | 6/1999 | Fukuda et al. |
| 6,171,586 B1 | 1/2001 | Lam et al. |
| 6,875,432 B2 | 4/2005 | Liu et al. |
| 2005/0175603 A1 | 8/2005 | Liu et al. |
| 2007/0116700 A1 | 5/2007 | Liu et al. |

FOREIGN PATENT DOCUMENTS

| | | |
|---|---|---|
| CA | 2448345 | 2/2010 |
| CH | 684 164 | 7/1994 |
| EP | 0 269 405 | 6/1988 |
| WO | WO 89/11297 | 11/1989 |
| WO | WO 89/11298 | 11/1989 |
| WO | WO 97/04801 | 2/1997 |
| WO | WO 97/45140 | 12/1997 |
| WO | WO 98/56418 | 12/1998 |
| WO | WO 99/01556 | 1/1999 |
| WO | WO 99/12522 | 3/1999 |
| WO | 02/30463 | 4/2002 |
| WO | WO 02/30463 | 4/2002 |

OTHER PUBLICATIONS

Cleland et al.,Critical Reviews in Therapeutic Drug Carrier Systems, 1993, 10(4):307-377.*
Reddy et al .,The Journal of immunology, 2000, vol. 164, p. 1925-1933.*
Rudikoff et al.,Proc Natl Acad Sci USA 1982 vol. 79, 1979-1983.*
Semotan et al., "A new method of preparation of bovine colostral immunoglobulins for parenteral administration in calves," PubMed Abstr. PMID:9441496 & Vet Med (Praha) vol. 42(9), pp. 249-252 (1997).
WPI Abstr. No. 1994-235212 & CH 684164 A (Rotkreuz. Zentrallab).
Powell et al., "Compendium of Excipients for Parenteral Formulations," Journal of Phrmaceutical Science & Technology, vol. 52(5), pp. 238-239 (1998).

* cited by examiner

*Primary Examiner*—Michael Szperka
*Assistant Examiner*—Yunsoo Kim
(74) *Attorney, Agent, or Firm*—Cozette M McAvoy; Leslie Fischer

(57) ABSTRACT

The present invention provides stable liquid formulations of antibodies suitable for parenteral administration. Also, provided are aqueous solutions which have high concentrations of therapeutic antibodies which may be used to produce therapeutical liquid formulations. The present invention also relates to uses, such as medical uses, of the stable liquid formulations and processes for the production of the stable liquid formulations.

44 Claims, No Drawings

STABLE LIQUID FORMULATIONS OF ANTIBODIES

This application is a continuation of U.S. application Ser. No. 10/478,630, filed Apr. 20, 2004, which is a 371 of PCT/EP02/06016, filed May 31, 2002.

PARTIES TO A JOINT RESEARCH AGREEMENT

Certain subject matter herein was developed during the course of a joint research agreement between Novartis Pharma AG and Genentech, Inc.

FIELD OF THE INVENTION

The present invention relates to aqueous solutions which have high concentrations of therapeutical antibodies and to stable liquid formulations which are based on such aqueous solutions of antibodies. The present invention also relates to uses, such as medical uses, of the stable liquid formulations and processes for the production of the stable liquid formulations.

BACKGROUND OF THE INVENTION

Stable liquid formulations of antibodies are useful for parenteral administration, such as intravenous (i.v.), intramuscular (i.m.) or subcutaneous (s.c.) administration. Such formulations must fulfill two key requirements: 1) the required drug concentration must be achieved, and, 2) the drug must be chemically and physically stable in order to have a sufficient shelf-life.

For a protein to remain biologically active, a formulation must preserve intact the Conformational integrity and at the same time the protein's multiple functional groups must be protected from degradation. Degradation pathways for proteins can involve chemical instability or physical instability. For example, chemical instability can result from deamidation, hydrolysis oxidation, beta-elimination or disulfide exchange, while physical instability can result from denaturation, aggregation, precipitation or adsorption, for example. Aggregation is one of the most common protein degradation pathways.

Most current stable formulations of antibodies are not liquid formulations. For example, WO97/04801 describes a stable lyophilized formulation of anti-IgE antibodies. The stability of proteins in aqueous formulations is of general importance to the pharmaceutical industry. The problem has been addressed by drying the protein, for example, by the method of freeze-drying. For a patient who needs daily injections of an antibody, it is of importance that the product is easy to handle, to dose and inject. Because a dried antibody formulation is then distributed and stored in dried form, the patient or medical professional has to reconstitute the dried powder in a solvent before use, which is an inconvenience for the patient.

Thus, it is advantageous to provide a liquid antibody formulation for which reconstitution before use is not required.

Furthermore, the freeze-drying process is a costly and time consuming process, and it would be advantageous if this step could be avoided when preparing a commercial antibody formulation.

It would also be advantage for the manufacture and formulation of a therapeutical product if the final pharmaceutical solution contained only few or no additives.

Thus, there is a demand on the market for stable, liquid, injectable antibody formulations; and, in particular, for highly concentrated stable, liquid, injectable antibody formulations.

There is also a need for stable aqueous solutions comprising a high concentration of antibody protein that can be used as a starting material or intermediate in process to obtain stable liquid antibody formulations of the invention.

BRIEF SUMMARY OF THE INVENTION

The present invention provides a stable aqueous solution comprising an antibody at a concentration of at least 50 mg/ml, and further comprising at least one acidic component.

Further, there is provided a suitable delivery system which contains the aqueous solution.

Further provided are the uses of the aqueous solution in a nasal spray or a slow release formulation.

Also provided is the use of the aqueous solution in a drying or freeze-drying process.

Stable aqueous solution are provided which can be used as an intermediate for the formulation of therapeutical formulations, e.g. further pharmaceutically acceptable components can be added to the aqueous solution in order to obtain the final therapeutical formulation. However, the stable aqueous solution of the invention can itself be used as a therapeutical formulation; i.e. including no or only few further additives.

Further components which may be added to the stable aqueous solution of the invention can be mere pharmaceutical additives which are not therapeutically active, or they can be therapeutically active substances. Also, by-products may or may not be present in the aqueous solutions of the invention. Accordingly, the stable aqueous solutions of the invention may either comprise, consist essentially of, or consist of an antibody at a concentration of at least 50 mg/ml and at least one acidic component.

Processes of making a therapeutical formulation employing the aqueous solution of the invention are also provided.

Thus, in one aspect of the invention a process is provided for the preparation of a therapeutical liquid formulation comprising an antibody, wherein in a first step an aqueous solution including an antibody at a concentration of at least 50 mg/ml and at least one acidic component is prepared; and, in a second step, at least one pharmaceutically acceptable additive is added to said aqueous solution.

Furthermore, a process is provided for the preparation of a therapeutical liquid formulation comprising an antibody at a concentration of more than 50 mg/ml, wherein in a first step an antibody solution in a suitable buffer is concentrated to between about 10 mg/ml and about 50 mg/ml; in a second step, the concentrated solution obtained in the first step is diafiltered with an aqueous solution of at least one acidic component, optionally containing $MgCl_2$ and/or $CaCl_2$ and/or further suitable additives; and, in a third step, the solution obtained in the second step is further concentrated to a concentration of more than 50 mg/ml.

Also provided is a process for the preparation of a therapeutical liquid formulation comprising an antibody at a concentration of more than 50 mg/ml, wherein
  in a first step an antibody solution in a suitable buffer is concentrated to a concentration of between about 10 mg/ml and about 50 mg/ml;
  in a second step, the concentrated solution obtained in the first step is diafiltered with an aqueous solution of at least one acidic component;"

in a third step, the solution obtained in the second step is further concentrated to an intermediate concentration of between about 100 and 200 mg/ml, preferably between about 100 and 150 mg/ml;

in a fourth step, the intermediate concentrated solution obtained in the third step is diafiltered with an aqueous solution of at least one acidic component and further containing $MgCl_2$ and/or $CaCl_2$ and/or further suitable additives, in a fifth step, the solution obtained in the fourth step is further concentrated to a concentration of more than 150 mg/ml.

DETAILED DESCRIPTION OF THE INVENTION

I. High Concentration Aqueous Solution of Antibody and Liquid Formulations

The present invention provides highly concentrated aqueous solutions of antibody and liquid formulations based thereon. The concentrated aqueous solutions of the invention include a therapeutical antibody and at least one acidic component. The aqueous solutions therefore generally have a pH below pH 7.0. They may or may not include further salts or additives. They may be used as an intermediate in a process to obtain a therapeutical liquid formulation of the invention, but they also may be suitable therapeutical liquid formulations themselves, i.e. without the addition of further pharmaceutically acceptable additives.

In one aspect the invention provides a stable aqueous solution comprising an antibody at a concentration of at least 50 mg/ml, and further comprising at least one acidic component. Preferred are concentrations of the antibody of at least 80 mg/ml, 100 mg/ml, 140 mg/ml, 160 mg/ml, 180 mg/ml, 200 mg/ml, 220 mg/ml, 250 mg/ml or even 300 mg/ml.

In developing a high concentration stable aqueous solution of antibody, the high viscosity of protein solutions has been identified as a major obstacle. For example, in physiological saline conditions or buffers at concentrations above 50 mg/ml antibody solutions, such as for example solutions of monoclonal antibody E25, can start to become viscous and/or turbid. The viscosity increases with protein concentration. The high viscosity of antibody solutions is a disadvantage from a medical point of view as, for example, reconstitution times may be as long as 30 min for an antibody lyophilizate. Further, after reconstitution and injection of a dry formulation about 30% of an antibody may be left in the vial and in the syringe, which severely increases the treatment cost.

The present invention now provides means to obtain a stable liquid pharmaceutical formulation comprising antibodies, such as anti-IgE antibodies, with a high protein concentration and a low viscosity.

Although we do not wish to be limited by any theoretical speculation, one phenomenon that may contribute to the observed viscosity of aqueous antibody solutions is the self-association of the antibody, or "aggregation". Antibody aggregates can be soluble or insoluble and both forms of aggregates can be covalent or non-covalent. The aggregates can give opalescent solutions, but there can also be non-visible aggregation which only can be shown chemically.

In addition to increasing viscosity, aggregation can be detrimental in several ways. For example, covalent aggregation in protein formulations may be essentially irreversible and could result in the production of inactive species, which in addition also may be immunogenic. Non-covalent aggregation can lead to loss of activity due to precipitation.

A "stable" aqueous solution or liquid formulation within the meaning of the invention is one in which the antibody therein essentially retains its physical and chemical stability and integrity upon storage. Various analytical techniques for measuring protein stability are available in the art. Stability can be measured at a selected temperature for a selected time period. For rapid screening, a formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 1 year. For example, in one preferred embodiment the aqueous solution of the invention has a stability of at least 1 year at about 4° C. The extent of viscosity and/or aggregation can be used as an indicator of protein stability. For example, a "stable" formulation may be one wherein less than about 10% and, preferably, less than about 5%, preferably less than about 2%, or even less than about 1% of the protein is present as an aggregate in the formulation. Aggregation can, for example, be measured by size exclusion chromatography.

The solutions of the invention are stable not only with regard to aggregation but also with regard to the chemical stability of the antibody. Chemical stability may, for example, be measured by hydrophobic interaction chromatography (HIC), for example by HIC-HPLC after papain digestion. For example, after storage of at least 1 year at about 4° C. the peak representing unmodified antibody in HIC-HPLC after papain digestion decreases no more than 20%, preferably no more than 10%, more preferably no more than 5% or even no more than 1%, as compared to the antibody solution prior to storage.

As the person skilled in the art will readily appreciate, there are other methods suitable to measure the stability of the solutions of the invention. For example, chemical stability may also be measured by capillary electrophoresis.

Chemical instability can impair the activity of the antibody in question. Examples of chemical instability are degradation of the antibody or changes in tertiary and/or quaternary structure of antibody molecules. In preferred embodiments the solutions and formulations of the invention lose less than 50%, preferably less than 30%, preferably less than 20%, more preferably less than 10% or even less than 5% or 1% of the antibody activity within 1 year storage under suitable conditions at about 4° C. The activity of an antibody can be determined by a suitable antigen-binding assay for the respective antibody.

The ability of an acidic component to produce a stable liquid antibody solution at high protein concentration can be determined by making up a solution including the acidic component to be tested and storing it for 24 hours at 22° C. For example, if after this time the solution remains clear the acidic component has stabilized the antibody and is one suitable for the use in an aqueous solution according to the present invention.

The degree of stability achieved depends on the acid used and on its concentration, the antibody concentration, and on the storage temperature. In general, the higher the concentration of the antibody and the higher the storage temperature, the shorter the time before aggregation occurs. In general higher antibody concentrations require higher concentrations of the acidic component.

Accordingly, it is found in the present invention that stable aqueous solutions and liquid formulations including antibodies having an acceptable viscosity for therapeutical applications can be made in the presence of specific acidic components.

Preferably, the viscosity of the aqueous solution or liquid formulation of the invention is below 200 mPa·s, preferably below 100 mPa·s, preferably below 70 mPa·s, more preferably below 50 mPa·s, more preferably below 20 mPa·s or even below 10 mPa·s at a shear rate of $\gamma=100$ (1/s). Another suitable shear rate to measure viscosity of antibody solutions is $\gamma=220$ (1/s).

Such reduced viscosity allows for a aqueous solution or liquid formulation of the invention having a higher concentration of the respective antibody. Thus, advantageously, the same amount of antibody may be administered in a smaller volume. Also, such smaller volume, advantageously, may allow to produce pre-filled delivery devices that include the entire therapeutical dosage of the respective antibody. Also, if small volumes can be used, a liquid formulation need not necessarily be isotonic to avoid pain to the patient. However, in one preferred embodiment the aqueous solution of the invention is isotonic. By "isotonic" it is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

According to the present invention the acidic component and the amount of acid being used is so chosen as to achieve the desired viscosity and stability of the high concentrated protein solution. Suitable acids that may be chosen include organic and inorganic acids. Organic acids of the invention may be carboxylic acids, such as monocarboxylic, dicarboxylic, tricarboxylic, tetracarboxylic, hydrocarboxylic acids or phenols. Weak organic acids are preferred acids of the present invention, for example monocarboxylic organic acids having a pK-value between 3.0 and 6.0, preferably between 4.5 and 5.0. Preferred examples of acidic components of the invention are acetic acid, citric acid, oxalic acid, succinic acid, tartaric acid, lactic acid, malic acid, glycolic acid and fumaric acid. In a particularly preferred embodiment the acidic component included in the aqueous solution is acetic acid.

Preferably, the pH of said aqueous solution or liquid formulation is above pH 3, for example between pH 3 and pH 7, more preferably it is between pH 3 and pH 6, more preferably between pH 4 and pH 6, or even between pH 5 and pH 6. In one preferred embodiment the pH is about pH 5.0 or about pH 6.0. Certain pH ranges are particularly preferred, for example, preferred is a pH below pH 6.0, or below pH 5.8, or below pH 5.6 or below pH 5.4, and a pH that is above pH 4.0, or above pH 4.2, or above pH 4.4, or above pH 4.6 or above pH 4.8, or above pH 5.0.

Preferably the acidic component of the invention, such as acetic acid, is present in a final concentration of at least 0.001%, preferably at least 0.01%, more preferably between 0.01%-0.2%. In one embodiment of the invention no additional buffering agent is present in the aqueous solution or liquid formulation of the invention. In another embodiment of the invention no sodium salt, such as for example sodium acetate is present in the aqueous solution or liquid formulation of the invention.

The concentration of the antibody, such as an anti-IgE antibody such as for example E25 (as defined hereinbelow), is above 50 mg/ml, for example it may be between 100 and 200 mg/ml and can go up to 300 mg/ml. Preferred is a concentration of at least 80, 100, 140, 160, 180, 200, 220, 250 or even 300 mg/ml. One preferred range is between 100 and 220 mg/ml for injectable solutions. If a protein shall be delivered via the nasal or even the oral route, preferred concentrations are at least 250 mg/ml or even 300 mg/ml, as high concentrations are particularly desirable for the delivery via the nasal or oral route.

The aqueous solution or liquid formulation of the invention may also contain more than one antibody as necessary for the particular indication being treated, preferably those with complementary activities that do not adversely affect the other antibody. The aqueous solution or liquid formulation herein may also include an additional therapeutical protein which is not an antibody. Such antibodies or proteins are suitably present in combination in amounts that are effective for the purpose intended. When including a further protein component in the aqueous solution, the total protein concentration should be taken into account when choosing the concentration of the acidic component.

In one aspect the present invention also provides for a stable aqueous solution consisting merely of an antibody at a concentration of at least 50 mg/ml and an acidic component. In another aspect the stable aqueous solution however may also consist essentially of an antibody at a concentration of at least 50 mg/ml and an acidic component, in particular it may further include by-product or therapeutically inactive additives.

Preferably, the aqueous solution or liquid formulation of the invention further includes $CaCl_2$ and/or $MgCl_2$. In a preferred embodiment the concentration of $CaCl_2$ is within the range of 50-200 mM, more preferably within 50-130 mM, preferably 100-130 mM, most preferably about 100 mM. In another preferred embodiment the concentration of $MgCl_2$ is within the range of 50-200 mM, more preferably within 50-130 mM, preferably 100-130 mM, most preferably about 100 mM. Stable aqueous solutions or liquid formulations including $MgCl_2$ are a particularly preferred embodiment of the present invention. In a further preferred embodiments these aqueous solutions or liquid formulations further include a detergent and/or a sugar.

II. Antibodies

The term "antibody" is used in a broad sense. The term "antibody" specifically covers monoclonal antibodies (including full length antibodies which have an immunoglobulin Fc region), antibody compositions with polyepitopic specificity, bispecific antibodies, diabodies, and single-chain molecules, as well as antibody fragments and/or derivatives such as, for example, Fab, $F(ab')_2$, and Fv fragments or other antigen-binding fragments. For example, an antibody derivative may be a PEGylated form of an antibody or antibody fragment.

In a preferred embodiment the antibody used in the aqueous solution of the invention has an isoelectric point between pH 6 and pH 8.

The term "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method or may be made by recombinant DNA methods. The "monoclonal antibodies" may also be isolated from phage antibody libraries.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain is identical with or homologous to corresponding sequences in antibodies derived from another species or belonging to another antibody class or subclass, as well as fragments of such antibodies, so long as they exhibit the desired biological activity.

"Humanized" forms of non-human antibodies are chimeric immunoglobulins, immunoglobulin chains or fragments thereof, such as Fv, Fab, Fab', F(ab')$_2$ or other antigen-binding subsequences of antibodies, which contain minimal sequence derived from non-human immunoglobulin. Usually, humanized antibodies are human immunoglobulins in which residues from a complementarity determining region (CDR) of the recipient are replaced by residues from a CDR of a non-human species. In some instances, Fv framework region residues of the human immunoglobulin are replaced by corresponding non-human residues. Also, complementarity determining region (CDR) residues originating from the non-human species may be replaced by corresponding human residues. Furthermore, humanized antibodies may comprise residues which are found neither in the recipient antibody nor in the imported CDR or framework sequences.

In a particularly preferred embodiment the antibody or antibody derivative is selected from anti-IgE antibodies, such as E25, E26, E27 (described in WO99/01556 as rhuMAbE-25, rhuMAbE-26, and rhuMAbE-27, respectively) or their fragments and derivatives. Preferably the anti-IgE antibody is a humanized murine antibody or a fully human antibody. Most preferably the anti-IgE antibody is Omalizumab, which is also named "E25". Another preferred anti-IgE antibody is named "E26" as further defined hereinbelow.

Generally, anti-IgE antibodies are described in the prior art, and in greater detail in the International applications WO 93/04173 and WO 99/01556. For example, WO 99/01556 specifically describes Omalizumab, also named E25, in FIG. 12, and in the sequences ID-No. 13-14. Antibody molecules comprising a E26 sequence are described in WO 99/01556 and are selected from the group of F(ab) fragment (Sequence ID Nos. 19-20), sFv fragment (Sequence ID No. 22) and F(ab)'$_2$ fragment (Sequence Nos. 24-25), in accordance to FIGS. 12-15. Within this invention, the terms E25 and E26 shall be construed accordingly. Preferably, the IgE antibodies of the instant invention do not result in histamine release from mast cells or basophils.

Furthermore, U.S. Pat. No. 5,449,760 generally describes anti-IgE antibodies that bind soluble IgE but not IgE on the surface of B cells or basophils. Antibodies such as these bind to soluble IgE and inhibit IgE activity by, for example, blocking the IgE receptor binding site, by blocking the antigen binding site and/or by simply removing the IgE from circulation. Additional anti-IgE antibodies and IgE-binding fragments derived from the anti-IgE antibodies are described in U.S. Pat. No. 5,656,273. U.S. Pat. No. 5,543,144 describes further anti-IgE antibodies that are suitable for this invention, in particular anti-IgE antibodies that bind soluble IgE and membrane-bound IgE on IgE-expressing B cells but not to IgE bound to basophils.

III. Aqueous Antibody Solutions Including Suitable Additives

Liquid Formulations

It has been surprisingly found that after the preparation of the highly-concentrated aqueous antibody acid solution according to the invention different ingredients can be added without a substantial increase in viscosity. The antibody acid solution can for example be mixed with sugars, detergents and/or other additives. Accordingly the present invention also describes methods suitable for the preparation of long-term stable liquid formulations of antibodies including such additives. Also provided are the aqueous solutions including such additives themselves.

A person skilled in the art will appreciate that a wide variety of excipients may be used as additives. Components that may be used as additives are e.g.:

a) liquid solvents, co-solvents, e.g. an alcohol, e.g. isopropanol, b) sugars or a sugar alcohols, e.g. mannitol, trehalose, sucrose, sorbitol, fructose, maltose, lactose or dextrans, c) detergents, e.g. TWEEN 20, 60 or 80 (polysorbate 20, 60 Or 80)

d) buffering agents, e.g. acetate buffer e) preservatives, e.g. benzalkonium chloride, benzethonium chloride, tertiary ammonium salts and chlorhexidinediacetate.

f) isotoning agents, e.g. sodium chloride g) carriers, e.g. polyethylene glycol (PEG), recombinant human serum albumin h) antioxidants e.g. ascorbic acid and methionine i) chelating agents e.g. EDTA j) biodegradable polymers e.g. polyesters k) salt-forming counterions e.g. sodium A "preservative" within the meaning of the invention is a compound which can be added to the diluent to essentially reduce bacterial action in the reconstituted formulation, thus facilitating the production of a multi-use reconstituted formulation, for example. For example, preservatives may advantageously be included in solutions suitable for nasal administration or in solutions for use with multiple pen injectors.

Preferred compounds to be added as further additives are detergents such as TWEEN 20, sugars such as sucrose, fructose, mannitol and preservatives. Preferably, additives derived from animal origin such as gelatine or serum albumin (e.g. BSA) are excluded from formulations of the invention. Please replace the second full paragraph of page 13 with the following paragraph:

Generally, acceptable additives are nontoxic to recipients at the dosages and concentrations employed. The formulations to be used for in vivo administration must be sterile. This is readily accomplished by filtration through sterile filtration membranes, alternatively, sterility of the entire mixture may be accomplished by autoclaving the ingredients, except for protein, at about 120° C. for about 30 minutes, for example.

The percentage of the acid solution and the amount of additives used can vary and depends on the intended use. For example during different manufacturing steps the concentration of the acid solution can differ from the concentration of the final product.

It should be noted that certain additives such as ethanol, phosphate buffer saline (PBS), or citrate buffer, may induce gelation, increased viscosity and/or aggregation of the antibody in question under certain pH conditions. If the problems cannot be avoided by routine changes in pH, such additives should preferably not be used for preparing compositions of this invention.

A liquid formulation may, for example, be made by adding the additives to an aqueous solution of the antibody and then stirring to dissolve. Any suitable stirrer may be used, e.g. a vortex mixer. It is preferred to dissolve the antibody in an aqueous solution of the acid and then to add an aqueous solution of the additives. The stirring may preferably be carried out under an inert gas atmosphere, such as nitrogen or argon, and the resulting solution may preferably be degassed under vacuum. The inert gas atmosphere and degassing both may help to prolong the stability of the solution. After preparation the solution may be stored in glass or plastics containers.

Preferably, the aqueous solution or liquid formulation of the invention further includes $CaCl_2$ and/or $MgCl_2$. In a preferred embodiment the concentration of $CaCl_2$ is within the range of 50-200 mM, more preferably 50-130 mM, preferably 100-130 mM, most preferably about 100 mM. In another preferred embodiment the concentration of $MgCl_2$ is within the range of 50-200 mM, more preferably 50-130 mM, preferably 100-130 mM, most preferably about 100 mM.

In one preferred embodiment the aqueous solution or liquid formulation of the invention further includes a detergent, such as for example TWEEN 20, TWEEN 60 or TWEEN 80.

In another preferred embodiment the aqueous solution or liquid formulation of the invention further includes at least one sugar. In a further preferred embodiment the aqueous solution or liquid formulation of the invention further includes at least one sugar selected from the group comprising trehalose, sucrose, mannitol, sorbitol, fructose, maltose, lactose or a dextran. However, in one embodiment of the invention the aqueous solution or liquid formulation of the invention does not include maltose.

In another embodiment the aqueous solution or liquid formulation of the invention further includes at least one buffering agent.

One desirable anti-IgE antibody aqueous solution discovered herein includes an anti-IgE antibody in amount between 100 and 200 mg/ml, preferably of about 190 mg/ml or of about 220 mg/ml, and $CaCl_2$ or $MgCl_2$ in an amount between 50 and 200 mM, preferably of about 50 mM or of about 100 mM, optionally a buffer and optionally a detergent, such as a Tween 20, e.g. at a concentration of about 0.02%. Preferably, this anti-IgE formulation is stable at 8° C. for at least 1 year.

IV. Devices

The aqueous solution or liquid formulation of the invention may, for example, be used with standard ampoules, vials, pre-filled syringes or multiple administration systems. In preferred embodiments, the aqueous solution may be administered to the patient by subcutaneous administration. For example, for such purposes, the formulation may be injected using a syringe. However, other injection devices for administration of the formulation are available such as injector pens, and subcutaneous patch delivery systems such as, for example, chip devices. However, the aqueous solution may also be administered to the patient by inhalation devices. Conventional systems for delivery of molecules through the nasal passages and the lung include metered dose inhalers, and liquid jet and ultrasonic nebulizers.

Accordingly, in one aspect the present invention also provides a delivery system which contains the aqueous solution selected from the group of single use injection syringes or inhalation devices.

The delivery system comprises a container. Suitable containers include, for example, bottles, vials (e.g. dual chamber vials), syringes (such as dual chamber syringes) and test tubes. The container may be formed from a variety of materials such as glass or plastic. The container holds the aqueous solution and the label on, or associated with, the container may indicate directions for use. The label may for example indicate that the aqueous solution is useful or intended for subcutaneous administration. The container holding the formulation may be a multi-use vial, which allows for repeat administrations (e.g. from 2-6 administrations) of the aqueous solution.

Accordingly, also provided is the use of the aqueous solution or liquid formulation according to the invention for the production of a delivery system for the use treatment of a disease.

In another embodiment of the invention, an article of manufacture is provided which contains the aqueous solution of the present invention and provides instructions for its use. Thus, an article of manufacture is provided herein which comprises:

a) container which holds a concentrated aqueous solution of an antibody; and b) instructions for diluting the concentrated aqueous solution with a diluent to a protein concentration in the diluted formulation of at least about 50 mg/mL. The article of manufacture may further comprise a second container which holds a diluent (eg. bacteriostatic water for injection comprising an aromatic alcohol).

The article of manufacture may further include other materials desirable from a commercial and user standpoint, including other buffers, diluents, filters, needles, syringes, and package inserts with instructions for use.

V. Specific Formulations

In another aspect of the invention there is provided a slow release formulation comprising the aqueous solution or liquid formulation of the invention. Preferred is a slow release formulation selected from the group of polymeric nano or microparticles, or from gels.

In a particularly preferred embodiment the slow release formulation is a gel such as a hyaluronic acid gel.

Besides convenience, slow release formulations offer other advantages for delivery of protein drugs including protecting the protein over an extended period from degradation or elimination, and the ability to deliver the protein locally to a particular site or body compartment thereby lowering overall systemic exposure.

The present invention, for example, also contemplates injectable depot formulations in which the protein is embedded in a biodegradable polymeric matrix. Polymers that may be used are the homo- and co-polymers of lactic and glycolic acid (PLGA). PLGA degrades by hydrolysis to ultimately give the acid monomers and is chemically unreactive under the conditions used to prepare, for example, microspheres and thus does not modify the protein. After subcutaneous or intramuscular injection, the protein is released by a combination of diffusion and polymer degradation. By using polymers of different composition and molecular weight, the hydrolysis rate can be varied thereby allowing release to last from days to months.

In a further aspect the present invention provides a nasal spray comprising the aqueous solution or liquid formulation of the present invention.

VI. Uses and Processes for Preparation

In a further aspect of the invention the use of an acidic component for the preparation of an aqueous solution comprising an antibody having a concentration of at least 50 mg/ml is provided.

Also provided is a process for the preparation of a aqueous solution according to the invention, which process comprises admixing an antibody with an acidic component.

Also provided is a process for the preparation of a therapeutical liquid formulation comprising an antibody, wherein in a first step an aqueous solution including an antibody at a concentration of at least 50 mg/ml and at least one acidic component is prepared, and, in a second step, at least one pharmaceutically acceptable additive is added to said aqueous solution.

Also provided is a process for the preparation of a therapeutical formulation including an antibody, which process comprises adding an acidic component on the last purification step of the preparation of said antibody. Such last step may, for example, be an elution step, a buffer exchange step or a step comprising continuous diafiltration.

Furthermore, a process is provided for the preparation of a therapeutical liquid formulation comprising an antibody at a concentration of more than 50 mg/ml, wherein in a first step an antibody solution in a suitable buffer is concentrated to a concentration between about 10 mg/ml and about 50 mg/ml; in a second step, the concentrated solution obtained in the first step is diafiltered with an aqueous solution of at least one acidic component, optionally containing $MgCl_2$ and/or $CaCl_2$ and/or further suitable additives; and, in a third step, the solution obtained in the second step is further concentrated to a concentration of more than 50 mg/ml.

For example, the aqueous solution of at least one acidic component may be a solution of acetic acid, such as a solution of between about 0.01% and about 0.1% acetic acid. $MgCl_2$ and/or $CaCl_2$ may be present at a concentration within the range of 50-200 mM, preferably 50-130 mM, more preferably 100-130 mM, most preferably about 100 mM. In a further preferred embodiments these aqueous solutions further include a detergent and/or a sugar.

Also provided is a process for the preparation of a therapeutical liquid formulation comprising an antibody at a concentration of more than 50 mg/ml, wherein in a first step an antibody solution in a suitable buffer is concentrated to a concentration of between about 10 mg/ml and about 50 mg/ml;

in a second step, the concentrated solution obtained in the first step is diafiltered with an aqueous solution of at least one acidic component;

in a third step, the solution obtained in the second step is further concentrated to an intermediate concentration of between about 100 and 200 mg/ml, preferably between about 100 and 150 mg/ml;

in a fourth step, the intermediate concentrated solution obtained in the third step is diafiltered with an aqueous solution of at least one acidic component containing $MgCl_2$ and/or $CaCl_2$ and/or further suitable additives; and, in a fifth step, the solution obtained in the fourth step is further concentrated to a concentration of more than 150 mg/ml.

The diafiltration is generally carried out at constant retentate volume, with at least 5 volumes, or preferably 8 volumes, of diafiltration buffer.

In a preferred embodiment a solution of $MgCl_2$ and/or $CaCl_2$ and/or further suitable additives may directly be added to the intermediate concentrated solution obtained in the third step of the above 5-step process. If $MgCl_2$ and/or $CaCl_2$ and/or further suitable additives are directly added, the fourth step (i.e. diafiltration with an aqueous solution of at least one acidic component containing $MgCl_2$ and/or $CaCl_2$ and/or further suitable additives) thereafter may be omitted if no further adjustment of the respective concentrations of the salts and/or additives is required. Generally, the 5-step process of the invention which adds the salts and/or additives only to an intermediate concentrated solution of antibody avoids the appearance of aggregates and/or turbidity in solutions of the process.

In one preferred embodiment, in the fourth step a concentrated aqueous solution of $MgCl_2$ (or $CaCl_2$), for example at concentration 1 M, is added directly into an ultrafiltration system, to give approximately the desired resulting concentration (for example 50 mM or 100 mM).

In preferred embodiments of the processes of the invention carboxylic acids, such as acetic acid, are employed as the acidic component. In preferred embodiments of these processes no salt of a carboxylic is added in the process. In particular, in these embodiments it is preferred if no salt of the corresponding carboxylic acid is added.

VII. Medical Uses

In one aspect, the present invention also provides the aqueous solution of the invention for use in medicine. In particular, the use of the aqueous solution for the manufacture of a medicament for the treatment of disease, such as for example an allergic disease, is provided.

The appropriate dosage of the protein will depend, for example, on the condition to be treated, the severity and course of the condition, whether the protein is administered for preventive or therapeutic purposes, previous therapy, the patient's clinical history and response to the protein, the type of antibody used, and the discretion of the attending physician. The antibody is suitably administered to the patient at one time or over a series of treatments and may be administered to the patient at any time from diagnosis onwards. The antibody may be administered as the sole treatment or in conjunction with other drugs or therapies useful in treating the condition in question.

The uses for a formulation including an anti-IgE antibody, for example, include the treatment or prophylaxis of IgE-mediated allergic diseases, parasitic infections, interstitial cystitis and asthma, in particular allergic asthma, allergic rhinitis and atopic dermatitis, for example. Depending on the disease or disorder to be treated, a therapeutically effective amount of the anti-IgE antibody may be administered to the patient.

In another aspect there is provided the use of the aqueous solution of the invention in a drying or freeze-drying process.

The invention will be more fully understood by reference to the following examples. They should not, however, be construed as limiting the scope of the invention.

EXAMPLES

Example 1

Solutions of 40 mg/ml E25 in the production buffer (10 mM histidine buffer 10% sucrose) were dialyzed against large volumes of water and of 0.01% acetic acid. The obtained E25 solutions, in water and in 0.01% acetic acid, were concentrated by filtration. The obtained E25 solution in water (99 mg/ml E25, pH 7.04) was much more viscous than the 0.01% acetic acid E25 solution (98 mg/ml E25, pH 5.4).

The beneficial effect of acetic acid in obtaining solutions with reduced viscosity was further documented. For example, 160 mg/ml E25 could be easily obtained in 0.1% acetic acid (final protein solution had a pH of 4.8) or solution of 183 mg/ml E25 in 0.01% acetic acid. A water solution of E25 of 170 mg/ml could also be prepared, but it was much more viscous than all the acetic acid solutions.

No chemical degradation was detected by capillary zone electrophoresis (CZE) after storing the solutions at 8° C. for 10 days.

Example 2

The buffer of a solution of 40 mg/ml E25 in the production buffer (10 mM histidine buffer 10% sucrose) was exchanged in a diafiltration equipment to 0.1% acetic acid. After that the E25 solution was concentrated by ultrafiltration to 161 mg/ml. The solution was fluid, no aggregation or opalescence was observed. The recovery was very good, about 95%. This solution of 161 mg/ml was further concentrated by filtration through centrifugation using Centricone tubes. Fluid, clear solutions of E25 in 0.1% acetic acid with concentrations of 214 mg/ml and also 297 mg/ml were obtained. The solutions can be easily handled through syringe needles and permit the development of a single use prefilled syringe with small volume (e.g., 0.5 ml to 1 ml).

Example 3

A solution of 40 mg/ml E25 in the final production buffer (containing 0.02% TWEEN 20) was dialyzed against 0.1% acetic acid. The resulted E25 solution in 0.1% acetic acid (still containing TWEEN 20 detergent) was concentrated by filtration through centrifugation using Centricone: a concentration of 243 mg/ml E25 was reached. The solution fluidity was similar to the fluidity of the solutions without TWEEN 20, showing that the detergent is compatible with the high protein concentrated formulation.

Example 4

The unexpected beneficial effect of acetic acid can be illustrated in the following experiment. Solutions of 161 mg/ml E25 in 0.1% (17.5 mM) acetic acid (pH 4.8) were dialyzed against i) 17.5 mM phosphate buffer with 145 mM NaCl (PBS) pH 7.4; ii) 17.5 mM acetate buffer pH 4.8; and iii) 17.5 mM citrate buffer pH 4.8. Unexpectedly, in the citrate buffer pH 4.8 solution E25 aggregated and the solution became white turbid. This did not happen in the other solutions. The phosphate buffer was more viscous than the acetate buffer solution. The phosphate buffer E25 solution became opalescent after one day at room temperature.

Example 5

The viscosity of different E25 solutions was measured. All measurements were performed with a Paar Physica cone and plate rheometer at 23° C. The results are shown in Table 1 and Table 2 below.

TABLE 1

| E25 Samples | Viscosity $\eta$ (mPa·s) at shear rate of $\gamma = 100$ (1/s) | Viscosity $\eta$ (mPa·s) at shear rate of $\gamma = 225$ (1/s) | Notes |
| --- | --- | --- | --- |
| 97.4 mg/ml, 0.01% acetic acid | 22.4 | 21.2 | Beneficial effect of 0.01% acetic acid compared to water |
| 99 mg/ml, in water | 33.9 | 32.0 | |
| 222 mg/ml, 0.1% acetic acid | 126 | 123 | |
| 222 mg/ml, 0.1% acetic acid, 50 mM CaCl2 | 66.6 | 63.2 | |
| 222 mg/ml, 0.1% acetic acid, 100 mM CaCl2 | 59.2 | 55 | $CaCl_2$ decreases the viscosity |
| 222 mg/ml, 0.1% acetic acid, 50 mM MgCl2 | 79.5 | 77.2 | |
| 222 mg/ml, 0.1% acetic acid, 100 mM MgCl2 | 67.9 | 64.5 | $MgCl_2$ decreases the viscosity |
| 222 mg/ml, 0.1% acetic acid, 50 mM NaCl | 109 | 103 | |
| 222 mg/ml, 0.1% acetic acid, 100 mM NaCl | 114 | 112 | |
| 222 mg/ml, 0.1% acetic acid, 150 mM NaCl | 117 | 118 | No effect of NaCl |

TABLE 2

| E25 Samples | Viscosity $\eta$ (mPa·s) at share rate of $\gamma = 1$ | Notes |
| --- | --- | --- |
| 222 mg/ml, 0.1% acetic acid | 368 | |
| 222 mg/ml, 0.1% acetic acid, 50 mM NaCl | 351 | |
| 222 mg/ml, 0.1% acetic acid, 100 mM NaCl | 1080 | |
| 222 mg/ml, 0.1% acetic acid, 150 mM NaCl | 2140 | NaCl increases the viscosity at very low shear rates |

Example 6

A solution of 161 mg/ml in 0.1% acetic acid was lyophilized in a glass vial.

After lyophilization the obtained E25 cake was difficult to solubilize with 0.1% acetic acid. However, the lyophilized E25 could be solubilized very quickly with a reconstitution solution of 0.1% acetic acid containing 100 mM $CaCl_2$. The lyophilized E25 was reconstituted at a concentration of 235 mg/ml. (the volume of the reconstitution solution was smaller than the initial volume of the solution). This example shows that CaCl$_2$ has unexpected beneficial effects in solubilizing E25 lyophilisates.

Example 7

General Method for the Preparation of High Concentrated Liquid Formulations The starting solution is a solution of purified antibody at low concentration (lower than the high concentrations of the invention) in an aqueous buffer, for example in the buffer resulting from the preceding process step (for example in the case of E25: 25 mM TRIS buffer pH 8 containing about 200 mM NaCl). The pH of this solution is adjusted to a value below the isoelectric point of the antibody, for example to pH 5, with an acid, for example with 5% acetic acid. The resulting solution is then concentrated and diafiltered by ultrafiltration, preferably in a tangential-flow filtration system, using a membrane able to retain quantitatively the antibody, for example with a cutoff of 30 kD or 10 kD.

In general the following 3-steps procedure applies:
- In a first step, the antibody solution is concentrated to an intermediate concentration, for example 40 mg/ml. Normally the retentate obtained is opalescent, due to antibody aggregation.
- In a second step, the concentrated solution is diafiltered with an aqueous acetic acid solution (for example 0.01% or 0.1% acetic acid) containing MgCl$_2$ or CaCl$_2$ (for example at concentration 50 mM or 100 mM) and optionally containing other additives (for example a sugar). The diafiltration is generally carried out at constant retentate volume, with at least 5 volumes, or preferably 8 volumes, of diafiltration buffer. During the diafiltration the antibody solution is turbid.
- In a third step, the diafiltered solution is further concentrated to a high concentration, for example higher or equal to 240 mg/ml. The final turbid retentate is then recovered out of the ultrafiltration system.

After an optional addition of additives (for example a detergent and eventually other excipients, e.g. sugars, buffering agents) and after filtration through a 0.2 µm filter, a high concentrated liquid formulation is obtained, which is clear and stable if stored at about 4° C.

In a preferred embodiment of this general method, in order to process less turbid solutions, the following 5-steps procedure applies:
- In a first step, the antibody solution is concentrated to an intermediate concentration, for example 40 mg/ml. Normally the retentate obtained is opalescent, due to antibody aggregation.
- In a second step, the concentrated solution is diafiltered with an aqueous solution containing only acetic acid (for example 0.01% or 0.1% acetic acid). The diafiltration is generally carried out at constant retentate volume, with at least 5 volumes, or preferably 8 volumes, of diafiltration buffer. Normally, a decrease of the turbidity is observed during the diafiltration and the solution turns clear.
- In a third step, the diafiltered solution is further concentrated to a higher intermediate concentration, preferably of about 120-130 mg/ml. Then, a concentrated aqueous solution of MgCl$_2$ (or CaCl$_2$), for example at concentration 1 M, is added directly into the ultrafiltration system, to give approximately the desired resulting concentration (for example 50 mM or 100 mM). After mixing by retentate recirculation, a decrease of the retentate pressure is observed, due to the resulting lower viscosity. The retentate obtained remains clear or slightly turbid.
- In a fourth step, the solution is diafiltered with the same acetic acid solution as used for the first diafiltration (for example 0.01% or 0.1% acetic acid), but this time containing additionally MgCl$_2$ (or CaCl$_2$) at the desired concentration (for example 50 mM or 100 mM), in order to adjust exactly this concentration in the retentate. The diafiltration is generally carried out at constant retentate volume, with at least 5 volumes, or preferably 8 volumes, of diafiltration buffer.
- In a fifth step, the diafiltered solution is further concentrated to a high concentration, for example higher or equal to 240 mg/ml. The final clear or slightly turbid retentate is then recovered out of the ultrafiltration system.

After an optional addition of additives (for example a detergent and eventually other excipients, e.g. sugars, buffering agents) and after filtration through a 0.2 µm filter, a high concentrated liquid formulation is obtained, which is clear and stable if stored at about 4° C.

Example 8

Preparation and Viscosity of a Formulation Containing Acetic Acid and MgCl$_2$ About 12 ml of the liquid formulation [257 mg/ml E25, 0.1% acetic acid, 50 mM MgCl$_2$] were prepared by ultrafiltration in a tangential-flow filtration system (membrane area: 150 cm$^2$, membrane cutoff: 10 kD, hold up volume of the system: 9 ml, retentate pressure: 2-3 bar), according to the 5-steps procedure described in Example 7.

The starting solution was a solution of purified E25 antibody at concentration 4.8 mg/ml in a 25 mM TRIS buffer pH 8 containing about 200 mM NaCl. After pH adjustment to pH 5 with 5% acetic acid, the following steps were carried out:
- In a first step, the solution was concentrated to 40 mg/ml.
- In a second step, the concentrated solution was diafiltered at constant retentate volume with 8 volumes of 0.1% acetic acid.
- In a third step, the diafiltered solution was concentrated to 127 mg/ml and, after retentate recirculation during 5 minutes with the filtrate line closed, a sample was taken for viscosity measurement. Then, an aqueous solution of 1 M MgCl$_2$ was added directly into the ultrafiltration system, to give approximately a resulting MgCl$_2$ concentration of 50 mM. After reconcentration to the initial retentate volume (i.e. the volume before the addition of MgCl$_2$) and after retentate recirculation during 3 minutes with the filtrate line closed, a sample of the retentate was taken for viscosity measurement.
- In a fourth step, the solution was diafiltered at constant retentate volume with 8 volumes of 0.1% acetic acid containing 50 mM MgCl$_2$.
- In a fifth step, the diafiltered solution was concentrated to about 260 mg/ml. After recovery of the retentate out of the ultrafiltration system and filtration through a 0.2 µm filter, a sample was taken for viscosity measurement. An other sample was diluted to 200 mg/ml with 0.1% acetic acid containing 50 mM MgCl$_2$, also for viscosity measurement.

The viscosity measurements of the samples were performed with a Paar Physica cone and plate rheometer at 23° C. and at a shear rate of 220 s$^{-1}$. The following results were obtained:

| Process step: | E25 conc. | pH | Viscosity |
|---|---|---|---|
| in 0.1% acetic acid, before MgCl$_2$ addition: | 127 mg/ml | 4.43 | 12.1 mPa · s |
| in 0.1% acetic acid, after MgCl$_2$ addition: | 127 mg/ml | 4.48 | 8.27 mPa · s |
| in 0.1% acetic acid, 50 mM MgCl$_2$: | 257 mg/ml | 3.84 | 135 mPa · s |
| in 0.1% acetic acid, 50 mM MgCl$_2$: | 200 mg/ml | 3.82 | 37.1 mPa · s |

Example 9

Viscosity of E25 Formulations Versus the Acetic Acid Concentration

The same experiment as stated in Example 8 was carried out several times, changing only the acetic acid concentration used for the diafiltration buffers, but keeping the final MgCl$_2$ concentration equal to 50 mM. The different high concentrated E25 solutions obtained were then diluted to about 200 mg/ml, using the respective diafiltration buffers (i.e. the corresponding acetic acid solutions containing 50 mM MgCl$_2$), for pH and viscosity measurements.

The viscosity measurements were performed with a Paar Physica cone and plate rheometer at 23° C. and at a shear rate of 220 s$^{-1}$. The following results were obtained:

| Formulation buffer: | E25 conc. | pH | Viscosity |
|---|---|---|---|
| 0.1% acetic acid, 50 mM MgCl$_2$: | 200 mg/ml | 3.82 | 37.1 mPa · s |
| 0.05% acetic acid, 50 mM MgCl$_2$: | 200 mg/ml | 4.03 | 31.4 mPa · s |
| 0.025% acetic acid, 50 mM MgCl$_2$: | 206 mg/ml | 4.26 | 33.8 mPa · s |
| 0.01% acetic acid, 50 mM MgCl$_2$: | 195 mg/ml | 4.63 | 38.3 mPa · s |
| 0.005% acetic acid, 50 mM MgCl$_2$: | 197 mg/ml | 4.83 | 54.5 mPa · s |
| 0.0025% acetic acid, 50 mM MgCl$_2$: | 205 mg/ml | 5.01 | 106 mPa · s |
| 0.001% acetic acid, 50 mM MgCl$_2$: | 201 mg/ml | 5.13 | 115 mPa · s |
| 0% acetic acid, 50 mM MgCl$_2$: | 198 mg/ml | 5.35 | 200 mPa · s |

As shown by these results, when lowering the acetic acid concentration from 0.1% to 0% (at constant antibody concentration and at constant. MgCl$_2$ concentration) the viscosity remains approximately constant in the concentration range between 0.1% and 0.01%, but increases drastically if the concentration is further reduced.

It was found that this "transition concentration" of about 0.0075% acetic acid corresponds to 1.3 mM, which corresponds to the E25 molar concentration corresponding to 200 mg/ml. Accordingly, in one embodiment of the invention the concentration of the acidic component of the invention is so chosen as to be about equal or above the molar concentration of the antibody of the aqueous solution or formulation of the invention.

Example 10

Viscosity of Formulations Containing Acetic Acid and Either MgCl$_2$ or CaCl$_2$ About 18 ml of the liquid formulation [237 mg/ml E25, 0.01% acetic acid, 50 mM MgCl$_2$] were prepared by ultrafiltration in a tangential-flow filtration system (membrane area: 150 cm$^2$, membrane cutoff: 10 kD, hold up volume of the system: 10 ml, retentate pressure: 2.5-4 bar), according to the 3-steps procedure described in Example 7:

The starting solution was a solution of purified E25 antibody at concentration 4.8 mg/ml in a 25 mM TRIS buffer pH 8 containing about 200 mM NaCl. After pH adjustment to pH 5 with 5% acetic acid, the following steps were carried out:
In a first step, the solution was concentrated to 40 mg/ml.
In a second step, the concentrated solution was diafiltered at constant retentate volume with 8 volumes of 0.01% acetic acid containing 50 mM MgCl$_2$.
In a third step, the diafiltered solution was concentrated to 230-240 mg/ml. After recovery of the retentate out of the ultrafiltration system and filtration through a 0.2 μm filter, two samples was taken for viscosity measurement (the first one as is, the second one after addition of 0.02% of TWEEN 20). Two other samples were diluted to about 210 mg/ml with 0.01% acetic acid containing 50 mM MgCl$_2$, also for viscosity measurement (the first one as is, the second one after addition of 0.02% of TWEEN 20).

The same experiment was repeated, but using CaCl$_2$ instead of MgCl$_2$, giving the liquid formulation [233 mg/ml E25, 0.01% acetic acid, 50 mM CaCl$_2$].

The viscosity measurements were performed with a Paar Physica cone and plate rheometer at 23° C. and at a shear rate of 220 s$^{-1}$. The following results were obtained:

| Formulation buffer: | E25 conc. | Viscosity |
|---|---|---|
| 0.01% acetic acid, 50 mM MgCl$_2$: | 237 mg/ml | 83.5 mPa · s |
| 0.01% acetic acid, 50 mM MgCl$_2$, 0.02% Tween 20: | 237 mg/ml | 86.6 mPa · s |
| 0.01% acetic acid, 50 mM CaCl$_2$: | 233 mg/ml | 60.5 mPa · s |
| 0.01% acetic acid, 50 mM CaCl$_2$, 0.02% Tween 20: | 233 mg/ml | 59.1 mPa · s |
| 0.01% acetic acid, 50 mM MgCl$_2$: | 211 mg/ml | 40.5 mPa · s |
| 0.01% acetic acid, 50 mM MgCl$_2$, 0.02% Tween 20: | 211 mg/ml | 42.1 mPa · s |
| 0.01% acetic acid, 50 mM CaCl$_2$: | 207 mg/ml | 34.8 mPa · s |
| 0.01% acetic acid, 50 mM CaCl$_2$, 0.02% Tween 20: | 207 mg/ml | 31.6 mPa · s |

As shown by these results, the viscosity values are slightly lower if CaCl$_2$ is used instead of MgCl$_2$. Moreover, the TWEEN 20 at concentration 0.02% has no influence on the viscosity.

Example 11

Preparation and Stability of High Concentrated Liquid Formulations

The three following high concentrated liquid formulations were prepared by ultrafiltration (about 65 ml each, starting with E25 drug substance without TWEEN), according to the 5-steps procedure described in Example 7:

| | Formulation # | | |
|---|---|---|---|
| | F1 | F2 | F3 |
| | | Lot # | |
| | NVP-IGE025-01PP01 | NVP-IGE025-01PP02 | NVP-IGE025-01PP03 |
| Composition: | | | |
| E25 | 196 mg/ml | 201 mg/ml | 167 mg/ml |
| acetic acid | 0.1% | 0.1% | 0.05% |

-continued

|  | Formulation # | | |
|---|---|---|---|
|  | F1 | F2 | F3 |
|  | Lot # | | |
|  | NVP-IGE025-01PP01 | NVP-IGE025-01PP02 | NVP-IGE025-01PP03 |
| $MgCl_2$ | 50 mM | 50 mM | 50 mM |
| Mg-acetate | — | 30 mM | 45 mM |
| Trehalose | 27 mg/ml | — | — |
| Tween 20 | 0.02% | 0.02% | 0.02% |
| pH | 4.50 | 4.95 | 5.20 |
| Tonicity | 273 mOsm/kg | 252 mOsm/kg | 277 mOsm/kg |
| Viscosity (at 220 $s^{-1}$; 23° C.) | 39.9 mPa·s | 48.3 mPa·s | 19.5 mPa·s |

These formulations were put on a stability program and were found to be stable after 6-months storage at 5° C. (study ongoing). The following assays were carried out: SEC (size-exclusion chromatography), HIC (hydrophobic-interaction chromatography after papain-digestion) and Bioassay (IgE-Receptor binding inhibition assay):

|  | Formulation # | | |
|---|---|---|---|
|  | F1 | F2 | F3 |
| SEC: | % Monomer: | % Monomer: | % Monomer: |
| start | 99.1 | 98.9 | 99.1 |
| 1 month (5° C.) | 98.5 | 98.6 | 98.6 |
| 3 months (5° C.) | 99.1 | 98.9 | 99.0 |
| 6 months (5° C.) | 98.7 | 98.3 | 98.7 |
| HIC: | % Unmodified: | % Unmodified: | % Unmodified: |
| start | 63 | 62 | 58 |
| 1 month (5° C.) | 63 | 62 | 63 |
| 3 months (5° C.) | 60 | 60 | 60 |
| 6 months (5° C.) | 59 | 61 | 62 |
| Bioassay: | % Specific Activity: | % Specific Activity: | % Specific Activity: |
| start | 105 | 107 | 100 |
| 1 month (5° C.) | 75 | 79 | 79 |
| 3 months (5° C.) | 97 | 95 | 99 |
| 6 months (5° C.) | 111 | 99 | 85 |

As shown by these results, the three liquid formulations have a stability of at least 6 months at 5° C.

Example 12

Viscosity of Aqueous Solutions of E25 at High Concentration Containing Only Acetic Acid at Low Concentration About 31 ml of the aqueous solution [127 mg/ml E25, 0.1% acetic acid] were prepared by ultrafiltration in a tangential-flow filtration system (membrane area: 150 cm², membrane cutoff: 10 kD, hold up volume of the system: 9 ml, retentate pressure: 2-3 bar), according to the three first steps of the 5-steps procedure described in Example 7:

The starting solution was a solution of purified E25 antibody at concentration 4.8 mg/ml in a 25 mM TRIS buffer pH 8 containing about 200 mM NaCl. After pH adjustment to pH 5 with 5% acetic acid, the following steps were carried out:

In a first step, the solution was concentrated to 40 mg/ml.

In a second step, the concentrated solution was diafiltered at constant retentate volume with 8 volumes of 0.1% acetic acid.

In a third step, the diafiltered solution was concentrated to about 120 mg/ml and a sample was taken for viscosity measurement.

The same experiment was carried out several times, changing only the acetic acid concentration used for the diafiltration.

The viscosity measurements were performed with a Paar Physica cone and plate rheometer at 23° C. and at a shear rate of 220 $s^{-1}$. The following results were obtained:

| Acetic acid concentration | E25 conc. | Viscosity |
|---|---|---|
| 0.1% (i.e. 17.3 mM) | 127 mg/ml | 12.1 mPa·s |
| 0.1% (i.e. 17.3 mM) | 111 mg/ml | 7.4 mPa·s |
| 0.05% (i.e. 8.7 mM) | 118 mg/ml | 9.4 mPa·s |
| 0.025% (i.e. 4.3 mM) | 121 mg/ml | 13.8 mPa·s |
| 0.01% (i.e. 1.7 mM) | 121 mg/ml | 17.8 mPa·s |
| 0.005% (i.e. 0.87 mM) | 120 mg/ml | 24.4 mPa·s |
| 0.0025% (i.e. 0.43 mM) | 115 mg/ml | 25.4 mPa·s |
| 0.001% (i.e. 0.17 mM) | 120 mg/ml | 26.7 mPa·s |
| 0% (i.e. water alone) | 116 mg/ml | 47.2 mPa·s |

As shown by these results, the beneficial effect of acetic acid compared to water is already observed at an acetic concentration as low as 0.17 mM, which allows to prepare an antibody solution at a concentration of 120 mg/ml having a viscosity significantly lower than 50 mPa·s (i.e. the corresponding viscosity obtained with water alone).

Example 13

Viscosity of Aqueous Solutions of E25 Containing Only 0.1% Acetic Acid, in Function of the Antibody Concentration The same experiment as stated in Example 12 was repeated using 0.1% acetic acid for the diafiltration step, but this time the diafiltered solution was concentrated to about 240 mg/ml (instead of 120 mg/ml). After recovery of the retentate out of the ultrafiltration system and filtration through a 0.2 µm filter, a sample was taken for viscosity measurement. Other samples were taken as well, for viscosity measurements after various dilution steps with 0.1% acetic acid.

The viscosity measurements were performed with a Paar Physica cone and plate rheometer at 23° C. and at a shear rate of 220 $s^{-1}$. The following results were obtained:

| Acetic acid conc. | E25 conc. | Viscosity |
|---|---|---|
| 0.1% | 240 mg/ml | 225 mPa·s |
| 0.1% | 220 mg/ml | 125 mPa·s |
| 0.1% | 200 mg/ml | 63 mPa·s |
| 0.1% | 180 mg/ml | 40 mPa·s |
| 0.1% | 170 mg/ml | 35 mPa·s |
| 0.1% | 148 mg/ml | 20 mPa·s |
| 0.1% | 127 mg/ml | 12 mPa·s |
| 0.1% | 85 mg/ml | 6 mPa·s |

As shown by these results, the beneficial effect of acetic acid allows to prepare antibody solutions at a concentration up to about 180 mg/ml, having a viscosity significantly lower than 50 mPa·s.

Example 14

Use of Citric Acid as Acidic Component

About 19 ml of an aqueous solution of E25 at a concentration of about 155 mg/ml in purified water having a pH of 4.4-4.6 adjusted with citric acid were prepared by ultrafiltration in a tangential-flow filtration system (membrane area: 150 cm$^2$, membrane cutoff: 10 kD, hold up volume of the system: 10 ml, retentate pressure: 2-3 bar), according to a procedure similar to the 3-steps procedure described in Example 7:

The starting solution was a solution of purified E25 antibody at concentration 4.8 mg/ml in a 25 mM TRIS buffer pH 8 containing about 200 mM NaCl. After pH adjustment to pH 4.7 with 0.5 M citric acid, corresponding to a resulting citric acid concentration of about 6.6 mM, the following steps were carried out:

- In a first step, H was tried to concentrate the solution to 40 mg/ml. But the filtrate flow decreased immediately very quickly, so that it was not possible to carry out this concentration step at the pH value of 4.7. In order to recover a normal filtrate flow, the pH of the solution was lowered by stepwise addition of small amounts of 0.5 M citric acid. Neither pH 4.4 nor pH 4.2 was low enough to allow a satisfactory filtrate flow. Finally, the concentration step was possible only after pH lowering to pH 4.0, corresponding to a resulting citric acid concentration of about 9 mM.
- In a second step, the concentrated solution was diafiltered at constant retentate volume with 8 volumes of purified water having a pH of about 4.4, preliminarily adjusted with a few droplets of 0.5 M citric acid, corresponding to a resulting citric acid concentration in the range of about 0.05 to 0.1 mM.
- In a third step, the diafiltered solution was concentrated as high as possible. After recovery of the retentate out of the ultrafiltration system and filtration through a 0.2 μm filter, a sample was taken for concentration and pH measurements.

The maximal reachable concentration was 155 mg/ml, with a resulting pH of 4.5. In comparison, the maximal concentration obtained by using 0.1% acetic acid (without other additives) with the same ultrafiltration equipment was about 240 mg/ml.

Moreover, a sample of this concentrated solution (155 mg/ml, pH 4.5) was taken for addition of sodium citrate buffer of pH 4.5 to a foreseen final buffer concentration of 17.5 mM. But already after the addition of the first droplets (of 1 M sodium citrate buffer pH 4.5), E25 aggregated immediately and the solution became white turbid, turning soon into a white solid gel. If 1 M MgCl$_2$ (instead of 1 M sodium citrate pH 4.5) is added to the final concentrated solution of Example 14 (to a final MgCl$_2$ concentration of 50 mM), the solution remains clear.

The invention claimed is:

1. A stable aqueous solution comprising an E25 anti-IgE antibody at a concentration of at least 80 mg/ml, and further comprising acetic acid at a concentration of at least 0.001%.

2. A stable aqueous solution comprising an E25 anti-IgE antibody at a concentration of at least 80 mg/ml and acetic acid, wherein the stable aqueous solution does not contain sodium acetate.

3. The stable aqueous solution of claim 1, wherein the acetic acid is present in a final concentration of at least about 0.01%.

4. The stable aqueous solution of claim 1 wherein the pH of said aqueous solution is above pH 3.

5. The stable aqueous solution of claim 1 wherein the pH of said aqueous solution is between pH 3 and about pH 6.

6. The stable aqueous solution of claim 1 wherein less than 5% of the E25 is present as aggregates after storage for at least 1 month at 30° C. and/or at least 1 year at about 4° C.

7. The stable aqueous solution of claim 1, further including CaCl$_2$.

8. The stable aqueous solution of claim 1, further including MgCl$_2$.

9. The stable aqueous solution of claim 1, further including at least one additive.

10. The stable aqueous solution of claim 9, wherein the additive is polysorbate.

11. The stable aqueous solution of claim 9, wherein the additive is a sugar.

12. The stable aqueous solution of claim 11, wherein the sugar is selected from the group consisting of trehalose, sucrose, mannitol, sorbitol, fructose, maltose, lactose and dextran.

13. The stable aqueous solution of claim 9, wherein the additive is a buffering agent.

14. The stable aqueous solution of claim 1 wherein said aqueous solution is isotonic.

15. A nasal spray comprising the stable aqueous solution as claimed in claim 1.

16. A slow release formulation comprising the stable aqueous solution as claimed in claim 1.

17. The slow release formulation of claim 16 selected from the group consisting of polymeric nanoparticles, polymeric microparticles, and gels.

18. The slow release formulation of claim 17, wherein the gel is a hyaluronic acid gel.

19. A delivery system which contains the aqueous solution as claimed in claim 1, selected from the group consisting of single use injection syringes and inhalation devices.

20. A process for the preparation of an aqueous solution according to claim 1, which process comprises admixing an E25 anti-IgE antibody with an acetic acid acidic component.

21. A process for the preparation of a therapeutic liquid formulation comprising an E25 anti-IgE antibody, wherein in a first step an aqueous solution including an E25 anti-IgE antibody at a concentration of at least 80 mg/ml and acetic acid at a concentration of at least 0.01% is prepared, and, in a second step, at least one pharmaceutically acceptable additive is added to said aqueous solution.

22. A process for the preparation of a therapeutic liquid formulation comprising an E25 anti-IgE antibody at a concentration of more than 80 mg/ml, wherein
- in a first step an E25 anti-IgE antibody solution in a suitable buffer is concentrated to a concentration of between about 10 mg/ml and 80 mg/ml;
- in a second step, the concentrated solution obtained in the first step is diafiltered with an aqueous solution of acetic acid, optionally containing MgCl$_2$ and/or CaCl$_2$ and/or further suitable additives; and,
- in a third step, the solution obtained in the second step is further concentrated to a concentration of more than 80 mg/ml.

23. A process for the preparation of a therapeutic liquid formulation comprising an E25 anti-IgE antibody at a concentration of more than 80 mg/ml, wherein
- in a first step an E25 anti-IgE antibody solution in a suitable buffer is concentrated to a concentration of between about 10 mg/ml and 80 mg/ml;

in a second step, the concentrated solution obtained in the first step is diafiltered with an aqueous solution of acetic acid;

in a third step, the solution obtained in the second step is further concentrated to an intermediate concentration of between about 100 and 150 mg/ml E25 anti-IgE antibody;

in a fourth step, the intermediate concentrated solution obtained in the third step is diafiltered with an aqueous solution of acetic acid and further containing $MgCl_2$ and/or $CaCl_2$ and/or further suitable additives; and, in a fifth step, the solution obtained in the fourth step is further concentrated to a concentration of more than 150 mg/ml E25 anti-IgE antibody.

24. The process of claim 23, wherein between the third and fourth step a solution of $MgCl_2$ and/or $CaCl_2$ and/or further suitable additives is directly added to the intermediate concentrated solution obtained in the third step.

25. The process of claim 20, wherein the acidic component is present in a final concentration of at least 0.001%.

26. The process of claim 20, wherein the pH of said aqueous solution is above pH 3.

27. The process of claim 20, wherein the pH of said aqueous solution is between pH 3 and about pH 6.

28. A therapeutic liquid formulation obtained by preparing an aqueous solution including an E25 anti-IgE antibody at a concentration of at least 80 mg/ml and acetic acid at a concentration of at least 0.01%; and adding at least one pharmaceutically acceptable additive to said aqueous solution.

29. The therapeutic liquid formulation of claim 28 wherein less than 5% of the E25 is present as aggregates after storage for at least 1 month at 30° C. and/or at least 1 year at about 4° C.

30. The therapeutic liquid formulation of claim 28, further including $CaCl_2$ at a concentration of between about 50 mM and 200 mM.

31. The therapeutic liquid formulation of claim 28, further including $MgCl_2$ at a concentration of between about 50 mM and 200 mM.

32. The therapeutic liquid formulation of claim 28, further including at least one additive.

33. The therapeutic liquid formulation of claim 32, wherein the additive is polysorbate.

34. The therapeutic liquid formulation of claim 32, wherein the additive is a sugar.

35. The therapeutic liquid formulation of claim 34, wherein the sugar is selected from the group consisting of trehalose, sucrose, mannitol, sorbitol, fructose, maltose, lactose and dextran.

36. The therapeutic liquid formulation of claim 32, wherein the additive is a buffering agent.

37. The therapeutic liquid formulation of claim 28, wherein said liquid formulation is isotonic.

38. A process for the preparation of a therapeutic liquid formulation comprising an anti-IgE E25 antibody, which process comprises adding acetic acid on the last purification step of the preparation of said antibody.

39. A stable aqueous solution, comprising: (i) an E25 anti-IgE antibody at a concentration of at least 80 mg/ml, (ii) acetic acid and (iii) $CaCl_2$ and/or $MgCl_2$.

40. The stable aqueous solution of claim 39, wherein the concentration of $CaCl_2$ is between about 50 mM and 200 mM.

41. The stable aqueous solution of claim 39, wherein the concentration of $MgCl_2$ is between about 50 mM and 200 mM.

42. The stable aqueous solution of claim 39, wherein the acetic acid is present in a final concentration of at least 0.001%.

43. The stable aqueous solution of claim 39, wherein the acetic acid is present in a final concentration of at least 0.01%.

44. A method of treating an allergic disease in a patient, comprising administering to the patient an effective amount of the stable aqueous solution according to claim 39.

* * * * *